United States Patent [19]

Marciel

[11] Patent Number: Plant 7,612

[45] Date of Patent: Aug. 6, 1991

[54] ROSE PLANT NAMED DEVMENTA

[75] Inventor: Stanley G. Marciel, Aptos, Calif.

[73] Assignee: DeVor Nurseries, Inc., Watsonville, Calif.

[21] Appl. No.: 456,848

[22] Filed: Dec. 18, 1989

[51] Int. Cl.[5] ..... A01H 5/00

[52] U.S. Cl. ..... Plt./12

[58] Field of Search ..... Plt. 12, 20, 21, 28, Plt./29

*Primary Examiner*—Howard J. Locker

*Attorney, Agent, or Firm*—Charles W. Rummler

[57] ABSTRACT

A new and distinct greenhouse rose particularly distinguished by its continuous and profuse production of relatively large flowers of a deep red color borne on strong upright stems of about 45 to 54 cm. in length on an upright bush having a vigorous, free-branching growth habit and abundant foliage.

1 Drawing Sheet

BACKGROUND OF THE NEW PLANT

This new plant originated as a seedling of an unknown hybrid of unknown parentage growing among a collection of miscellaneous rose plants maintained for breeding purposes. This plant caught my attention because of its overall bright red color, its relatively large size on strong upright stems of a plant having good foliage and an apparently vigorous growth habit. Because of those characteristics, I propagated this seedling at Pleasanton, Calif. by budding with very satisfactory results whereupon I continued propagating this plant in the same manner through several generations in greenhouse at Pleasanton which demonstrated conclusively that the novel characteristics of the discovery seedling would hold true from generation to generation and appeared to be firmly fixed.

DESCRIPTION OF THE DRAWING

This new rose plant is illustrated by the accompanying full color photographic drawing which shows a group of the flowers in various stages of development, the colors shown being as nearly true to that herein specified as is reasonably possible to obtain by conventional photographic procedures.

DESCRIPTION OF THE NEW VARIETY

The following is a detailed description of my new greenhouse rose plant based upon observation of plants grown in greenhouse at Watsonville, Calif., with the color designations being according to The R.H.S. Colour Chart published by The Royal Horticultural Society of London, England.

THE PLANT

Origin: Seedling.
Parentage: Unknown.
Classification:
*Botanic.*—Hybrid Rose.
*Commercial.*—Greenhouse Rose Plant.
Form: Upright bush.
Growth: Vigorous, very sturdy, upright and free branching.
Height: About 75 cm.
Main stem length: About 45 to 54 cm.
Color: 146-B.
Foliage:

*Quantity.*—Abundant.
*Number of leaves.*—About 8 in average from the last flower cut.
*Shape of leaf.*—Odd pinnate.
*Size.*—About 132 mm. long and about 9.5 cm. wide.
*Leaflets.*—Number: 5 or 7. Size: Average about 62 mm. long and about 39 mm. wide. Shape: Ovate with serrated margins. Texture: Leathery. Aspect: Smooth and semi-glossy. Color: Upper side — Yellow-green 147-A. Under side — Greyed green 191-B with touches of Greyed purple 186-B. Stipules: Serrated adnate. Petiolule: 1 mm. long. Petioles: Length: About 20 mm. Ribs and veins: Slightly depressed on upper side and rounded on under side. Rachis: Smooth with small spines underneath.

Thorns:
*Number.*—Average.
*Size.*—About 10 mm. long.
*Color.*—Greyed red 178-A.

THE BUD

Size: Medium size commercial bud.
*Diameter.*—About 40 mm.
*Length.*—About 34 mm.
Shape: Tapering.
Opening rate: Slow.
Color of petals:
*When sepals first divide.*—Red 46-A.
*When petals begin to unfurl.*—Red purple 57-A.
Sepals:
*Number.*—Five.
*Shape.*—Branching with small leafs protruding on each side.
*Character.*—Sepals curl back when the flower opens.
*Color.* —Inside— Yellow-green 147-C. Outside — Yellow-green 144-A.
Calyx:
*Shape.*—Funnel-shaped.
*Size.*—Medium.
*Splitting.*—Calyx does not split.
*Aspect.*—Smooth.
Peduncle:
*Length.*—About 53 mm.
*Character.*—Hairy, rigid and erect.
*Color.*—Yellow-green 146-C.

THE FLOWER

Blooming habit: Continuous and profusely, from early Spring through Fall, blooming freely under greenhouse conditions.

Size of bloom: Large.

*Diameter.*—About 54 mm.

*Depth.*—About 36 mm.

Borne: Singly.

Shape:

*When bloom first opens.*—Cup shaped with high center.

Petalage:

*Number.*—About 24.

*Arrangement.*—Imbricated.

*Form.*—Ovoid with wide mucronate apex.

*Texture.*—Soft.

*Aspect.*—Velvety.

*Color.*—Outer petals body — Currant Red 46-A. Base — Yellow-green 154-D. Reverse side — Red Purple 63-B. Inside petals: Body — Currant Red 46-A. Base — Yellow 2-C. Reverse side — Red Purple 63-B. Base — Yellow 2-D.

Petaloids:

*Number.*—About 6.

*Size.*—17 mm.

*Color.*—Red 46-A.

Fragrance: Slight.

Discoloration after full bloom: Slight.

Persistance: The flowers hang on and dry.

Lasting quality: Long lasting both on plant and as a cut flower.

Disease resistance: Moderately resistant to mildew, black spots and rust as observed at Pleasanton, Calif.

THE REPRODUCTIVE ORGANS

Stamens:

*Number.*—About 107.

*Arrangement.*—Introse.

*Anthers.*—Size: About 3 mm. Color: Yellow-orange 20-B.

*Filaments.*—Length: About 8 mm. Color: Yellow 5-B.

*Pollen.*—Color: Yellow-orange 20-B.

Pistils:

*Number.*—About 49.

*Styles.*—Length: About 9 mm. Color: Yellow-green 154-C.

*Stigmas.*—Color: Yellow-orange 16-B.

Character of the ovaries: Oval shaped, slightly flattened.

THE FRUIT

Fertility: The fruit is fertile.

Size: Medium.

Shape: Round.

Color: Greyed Orange 167-C.

I claim:

1. The new and distinct variety of greenhouse rose substantially as herein shown and described, particularly characterized by its continuous and profuse production of relatively large flowers having a Currant Red coloration, the plant being further distinguished by its vigorous free branching growth habit with abundant foliage.

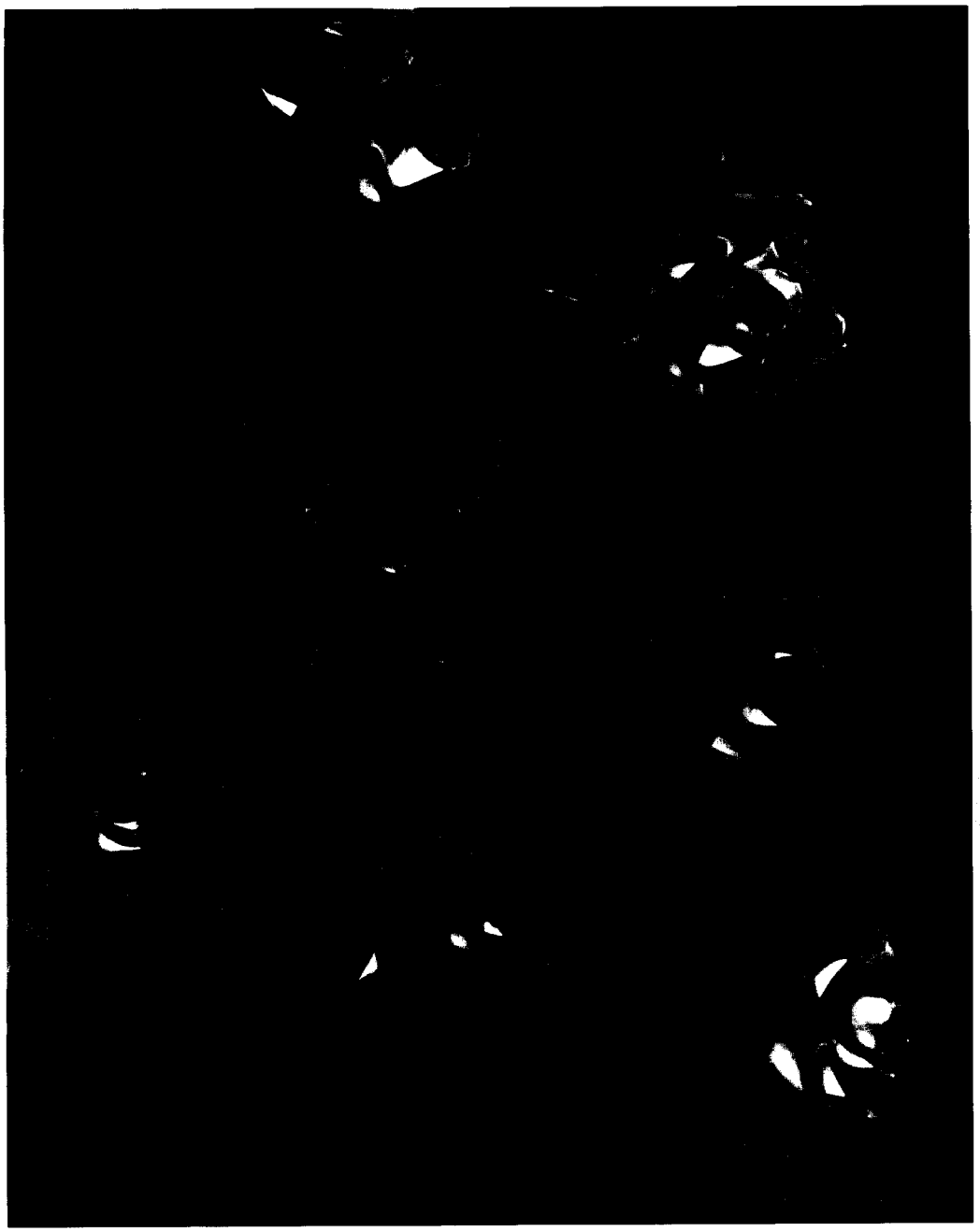

* * * * *